United States Patent
Nielsen et al.

(10) Patent No.: US 7,993,900 B2
(45) Date of Patent: Aug. 9, 2011

(54) SUBTILASES

(75) Inventors: Preben Nielsen, Horsholm (DK); Poul Erik Pedersen, Farum (DK); Helle Outtrup, Vaerloese (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 12/856,964

(22) Filed: Aug. 16, 2010

(65) Prior Publication Data

US 2010/0311635 A1 Dec. 9, 2010

Related U.S. Application Data

(62) Division of application No. 11/575,544, filed as application No. PCT/DK2005/000598 on Sep. 21, 2005, now Pat. No. 7,811,979.

(60) Provisional application No. 60/611,592, filed on Sep. 21, 2004.

Foreign Application Priority Data

Sep. 21, 2004 (DK) ................................. 2004 01430

(51) Int. Cl.
*C12N 9/50* (2006.01)
*C12N 15/00* (2006.01)
*C12N 1/20* (2006.01)
*C07K 1/00* (2006.01)

(52) U.S. Cl. .................. 435/219; 435/252.3; 435/320.1; 536/23.1; 530/350

(58) Field of Classification Search .................. 435/219, 435/320.1, 25.3; 536/23.1; 530/350
See application file for complete search history.

(56) References Cited

U.S. PATENT DOCUMENTS

| 5,891,701 | A | 4/1999 | Sloma et al. |
| 6,376,227 | B1 | 4/2002 | Takaiwa et al. |
| 7,101,698 | B2 * | 9/2006 | Sato et al. ..................... 435/221 |
| 7,727,756 | B2 * | 6/2010 | Svendsen et al. ............. 435/219 |
| 2004/0072321 | A1 | 4/2004 | Sato et al. |
| 2008/0318271 | A1 | 12/2008 | Nielsen et al. |

FOREIGN PATENT DOCUMENTS

| EP | 1 029 920 | 8/2000 |
| EP | 1 209 233 | 5/2002 |
| JP | 4-197182 | 7/1992 |
| WO | WO 88/01293 | 2/1988 |
| WO | WO 92/17577 | 10/1992 |
| WO | WO 98/56927 | 12/1998 |
| WO | WO 2004/067737 | 8/2004 |
| WO | WO 2006/032278 | 3/2006 |

OTHER PUBLICATIONS

English language abstract of JP7-62152 available as Derwent Primary Accession No. 1988-164153 to Lion Corp, Patent Nos. JP63101491-A; JP95062152-B2 (2 pages).
Karl-Heinz Maurer et al, Current Opinion in Biotechnology, vol. 15, pp. 330-334 (2004).
Saeki et al, Biochemical and Biophysical Research Communications, vol. 279, pp. 313-319 (2000).
Siezen et al, Protein Science, vol. 6, pp. 501-523 (1997).
XP-002354927, Accession # AB084155 (Abstract)(2003).

* cited by examiner

*Primary Examiner* — Maryam Monshipouri
(74) *Attorney, Agent, or Firm* — Kristin J. McNamara

(57) ABSTRACT

The present invention relates to novel JP170 like subtilases from wild-type bacteria, hybrids thereof and to methods of construction and production of these proteases. Further, the present invention relates to use of the claimed subtilases in detergents, such as a laundry or an automatic dishwashing detergent.

20 Claims, 2 Drawing Sheets

Phylogenetic tree

|  | CDJ120 | D6 | JP170 | KAO-A1 | KSM-KP43 | KSM-KP9860 | KSM-KP9865 | JP170/CDJ120 | ProtY |
|---|---|---|---|---|---|---|---|---|---|
| D6 | 86,8 | | | | | | | | |
| JP170 | 92,9 | 88,9 | | | | | | | |
| KAO-A1 | 92,9 | 88,5 | 91,9 | | | | | | |
| KSM-KP43 | 97,7 | 87,5 | 93,5 | 93,5 | | | | | |
| KSM-KP9860 | 96,1 | 88,2 | 93,1 | 92,4 | 96,5 | | | | |
| KSM-KP9865 | 97,9 | 87,8 | 93,8 | 93,8 | 99,8 | 96,8 | | | |
| JP170/CDJ120 | 97,9 | 88 | 94,7 | 92,9 | 97,9 | 95,9 | 98,2 | | |
| ProtY | 86,6 | 98,8 | 88,7 | 88 | 87,5 | 88,2 | 87,8 | 88 | |
| SD521 | 87,1 | 99,3 | 89,1 | 88,7 | 88 | 88,7 | 88,2 | 88,5 | 99,1 |

Fig. 2

Identity matrix

SUBTILASES

CROSS-REFERENCE TO RELATED APPLICATIONS

This application is a divisional of U.S. application Ser. No. 11/575,544 filed on Mar. 19, 2007 (now U.S. Pat. No. 7,811,979) which is a 35 U.S.C. 371 national application of PCT/DK2005/000598 filed Sep. 21, 2005, which claims priority or the benefit under 35 U.S.C. 119 of Danish application no. PA 2004 01430 filed Sep. 21, 2004 and U.S. provisional application No. 60/611,592 filed Sep. 21, 2004 the contents of which are fully incorporated herein by reference.

SEQUENCE LISTING AND DEPOSITED MICROORGANISMS

Sequence Listing

The present invention comprises a sequence listing.
Deposit of Biological Material
The following biological material has been deposited under the terms of the Budapest Treaty with the Deutsche Sammlung von Mikroorganismen and Zellkulturen and given the following accession number:

| Deposit | Accession Number | Date of Deposit |
| --- | --- | --- |
| JP170/CDJ120 hybrid | DSM16711 | 15 Sep. 2004 |
| CDJ120 mature | DSM16721 | 15 Sep. 2004 |

The deposit DSM16711 contain a plasmid comprising a fragment of DNA encoding the open reading frame of the hybrid subtilase gene (JP170/CDJ120 hybrid), whereas the deposit DSM16721 contain a plasmid comprising a fragment of DNA encoding the mature segment the subtilase gene (CDJ120).

FIELD OF THE INVENTION

The present invention relates to novel JP170 like subtilases from wild-type bacteria, hybrids thereof and to methods of construction and production of these proteases. Further, the present invention relates to use of the claimed subtilases in detergents, such as a laundry detergent or an automatic dishwashing detergent.

BACKGROUND OF THE INVENTION

Enzymes have been used within the detergent industry as part of washing formulations for more than 30 years. Proteases are from a commercial perspective the most relevant enzyme in such formulations, but other enzymes including lipases, amylases, cellulases, hemicellulases or mixtures of enzymes are also often used.

The search for proteases with appropriate properties include both discovery of naturally occurring proteases, i.e. so called wild-type proteases but also alteration of well-known proteases by e.g. genetic manipulation of the nucleic acid sequence encoding said proteases. One family of proteases, which is often used in detergents, is the subtilases. This family has been further grouped into 6 different subgroups (Siezen R. J. and Leunissen J. A. M., 1997, Protein Science, 6, 501-523). One of these sub-groups, the Subtilisin family was further divided into the subgroups of "true subtilisins (I-S1)", "high alkaline proteases (I-S2)" and "intracellular proteases". Siezen and Leunissen identified also some proteases of the subtilisin family, but not belonging to any of the subgroups. The true subtilisins include proteases such as subtilisin BPN'(BASBPN), subtilisin Carlsberg (ALCALASE®, NOVOZYMES A/S) (BLSCAR), mesentericopeptidase (BMSAMP) and subtilisin DY (BSSDY). The high alkaline proteases include proteases such as subtilisin 309 (SAVINASE®, NOVOZYMES A/S) (BLSAVI) subtilisin PB92 (BAALKP), subtilisin BL or BLAP (BLSUBL), subtilisin 147 (ESPERASE®, NOVOZYMES A/S), subtilisin Sendai (BSAPRS) and alkaline elastase YaB. Outside this grouping of the subtilisin family a further subtilisin subgroup was recently identified on the basis of the 3-D structure of its members, the TY145 like subtilisins. The TY145 like subtilisins include proteases such as TY145 (a subtilase from *Bacillus* sp. TY145, NCIMB 40339 described in WO 92/17577) (BSTY145), subtilisin TA41 (BSTA41), and subtilisin TA39 (BSTA39).

The JP170 subtilase type was first described as protease A in WO 88/01293 to Novozymes A/S disclosing four strains producing this type of protease. Later U.S. Pat. No. 5,891,701 to Novozymes Biotech disclosed the amino acid sequence of JP170 and the DNA sequence encoding it. The patents JP7-62152 and JP 4197182 to Lion Corp. disclosed the alkaline protease Yb produced by *Bacillus* sp. Y that is homologous to JP170 and the DNA sequence encoding Yb. *Bacillus* sp. Y also produces the protease Ya (Geneseq P entry AAR26274). And in addition U.S. Pat. No. 6,376,227 to Kao Corp. discloses physical characteristics as well as DNA and polypeptide sequences of alkaline proteases KP43, KP1790 and KP9860 which are also homologous to JP170. Recently genetic engineered variants of the KP43, KP9860 and Ya proteases among others were disclosed in EP 1 209 233, which also disclosed protease A-2 from *Bacillus* sp. NCIB12513. Kao Corp. also disclosed the proteases KSM-KP9865 and A-1 in US 2004/072321. Other known proteases belonging to this group are Protease E-1 derived from *Bacillus* sp. strain No. D6 (FERM P-1592), JP7407101, Protease SD521 derived from *Bacillus* sp. strain SD-521 (FERM BP-11162), JP9108211, and protease A1 derived from NCIB12289, WO 88/01293 to Novozymes A/S.

BRIEF DESCRIPTION OF THE INVENTION

The inventors have isolated novel proteases belonging to the JP170 like proteases subgroup of the subtilisin family that possess advantageous properties, such as improved detergent stability.

Furthermore the inventors have inserted truncated forms of the genes encoding various members of this subgroup into the gene encoding the JP170 protease thereby creating hybrid JP170 like proteases exhibiting improved performance in comparison to the JP170 protease.

The invention therefore in a further embodiment provides hybrid protease.

BRIEF DESCRIPTION OF DRAWINGS

FIG. 2, Matrix with amino acid sequence identities of the enzymes of the invention and the closest prior art known to the applicant.

DEFINITIONS

Figure 1:
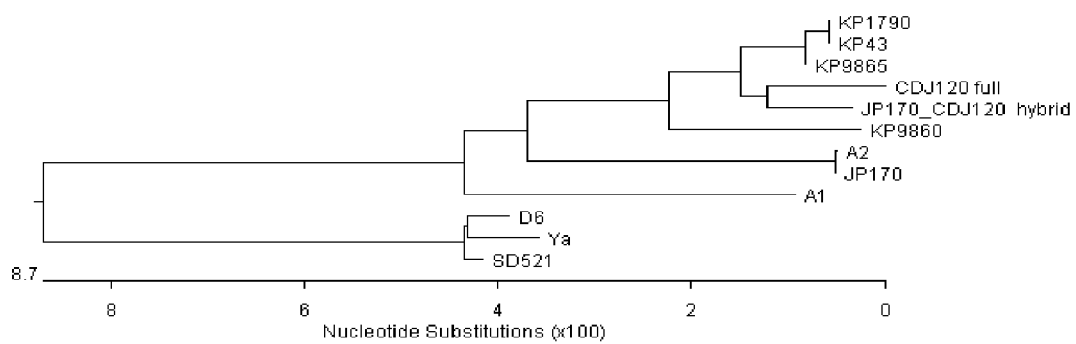
FIG. 1, Phylogenetic tree showing the relationship of the mature subtilase peptide sequences were constructed upon alignment with default settings in the ClustalW function of program MegAlign™ version 5.05 in DNAStar™ program package.

Prior to discussing this invention in further detail, the following terms and conventions will first be defined.

For a detailed description of the nomenclature of amino acids and nucleic acids, we refer to WO 00/71691 page 5, hereby incorporated by reference. A description of the nomenclature of modifications introduced in a polypeptide by genetic manipulation can be found in WO 00/71691 page 7-12, hereby incorporated by reference.

The term "subtilases" refer to a sub-group of serine proteases according to Siezen et al., *Protein Engng.* 4 (1991) 719-737 and Siezen et al. *Protein Science* 6 (1997) 501-523. Serine proteases or serine peptidases is a subgroup of proteases characterised by having a serine in the active site, which forms a covalent adduct with the substrate. Further the subtilases (and the serine proteases) are characterised by having two active site amino acid residues apart from the serine, namely a histidine and an aspartic acid residue.

The subtilases may be divided into 6 sub-divisions, i.e. the Subtilisin family, the Thermitase family, the Proteinase K family, the Lantibiotic peptidase family, the Kexin family and the Pyrolysin family.

The Subtilisin family (EC 3.4.21.62) may be further divided into 3 sub-groups, i.e. I-S1 ("true" subtilisins), I-S2 (highly alkaline proteases) and intracellular subtilisins. Definitions or grouping of enzymes may vary or change, however, in the context of the present invention the above division of subtilases into sub-division or sub-groups shall be understood as those described by Siezen et al., *Protein Engng.* 4 (1991) 719-737 and Siezen et al. *Protein Science* 6 (1997) 501-523.

The term "parent" is in the context of the present invention to be understood as a protein, which is modified to create a protein variant. The parent protein may be a naturally occurring (wild-type) polypeptide or it may be a variant thereof prepared by any suitable means. For instance, the parent protein may be a variant of a naturally occurring protein which has been modified by substitution, chemical modification, deletion or truncation of one or more amino acid residues, or by addition or insertion of one or more amino acid residues to the amino acid sequence, of a naturally-occurring polypeptide. Thus the term "parent subtilase" refers to a subtilase which is modified to create a subtilase variant.

The term "hybrid" is in the context of this invention to be understood as a protein that has been modified by replacing one or more segments of the gene encoding the parent protein with corresponding segments derived from genes encoding another protein.

The term "core" in the context of this invention is to be understood as a segment that comprises a substantial part of the subtilase gene including the part encoding the active site and a substantial part of the rest of the subtilase molecule, to provide unique traits to a hybrid.

The term "modification(s)" or "modified" is in the context of the present invention to be understood as to include chemical modification of a protein as well as genetic manipulation of the DNA encoding a protein. The modification(s) may be replacement(s) of the amino acid side chain(s), substitution(s), deletion(s) and/or insertions in or at the amino acid(s) of interest. Thus the term "modified protein", e.g. "modified subtilase", is to be understood as a protein which contains modification(s) compared to a parent protein, e.g. subtilase.

"Homology" or "homologous to" is in the context of the present invention to be understood in its conventional meaning and the "homology" between two amino acid sequences should be determined by use of the "Similarity" defined by the GAP program from the University of Wisconsin Genetics Computer Group (UWGCG) package using default settings for alignment parameters, comparison matrix, gap and gap extension penalties. Default values for GAP penalties, i.e. GAP creation penalty of 3.0 and GAP extension penalty of 0.1 (Program Manual for the Wisconsin Package, Version 8, August 1994, Genetics Computer Group, 575 Science Drive, Madison, Wis., USA 53711). The method is also described in S. B. Needleman and C. D. Wunsch, Journal of Molecular Biology, 48, 443-445 (1970). Identities can be extracted from the same calculation. The homology between two amino acid sequences can also be determined by "identity" or "similarity" using the GAP routine of the UWGCG package version 9.1 with default setting for alignment parameters, comparison matrix, gap and gap extension penalties can also be applied using the following parameters: gap creation penalty=8 and gap extension penalty=8 and all other parameters kept at their default values. The output from the routine is besides the amino acid alignment the calculation of the "Percent Identity" and the "Similarity" between the two sequences. The numbers calculated using UWGCG package version 9.1 is slightly different from the version 8.

The term "position" is in the context of the present invention to be understood as the number of an amino acid in a peptide or polypeptide when counting from the N-terminal end of said peptide/polypeptide. The position numbers used in the present invention refer to different subtilases depending on which subgroup the subtilase belongs to.

DETAILED DESCRIPTION OF THE INVENTION

Construction of Degenerated Primers

Degenerated primers were constructed from an alignment of genes of already known proteases such as Ya, KAO KSM-43 and JP170. The primers were degenerated in order to allow screening for protease gene fragments different from Ya, KAO KSM-43 and JP170.

PCR Screening

From the company culture collection a selection of bacterial strains were included in a PCR screening using the primers SF16A767F and SF16A1802R. The expected size of the PCR product was 1050 nucleotides. All PCR products of the expected size were sequenced in two sequence reaction using one of each of the same two primers. The nucleotide sequences were translated to amino acid sequences, and the diversity analysed by comparative peptide sequence analysis.

Based on the results of the screening a number of enzymes were selected for further investigation. The selected enzymes are shown in FIG. 1, and they both represent new enzyme molecules and representatives of the prior art. The enzyme selected for further investigation is CDJ120 which can be seen as forming a separate group in FIG. 1. Also hybrid subtilases produced as described below can be seen in FIG. 1.

Based on these results the inventors decided to move on with a dual approach; expression of the PCR product by in frame fusions to N and C terminal parts of the known protease of *Bacillus halmapalus* strain JP170 and inverse PCR to get the full sequences of selected enzymes.

Expression of Hybrid Proteases

Description of SOE PCR

By SOE PCR (SOE: Splicing by Overlapping Extension) hybrid gene products comprising 5 segments were generated as described in Example 2. The hybrid subtilase genes are used for production of a mature protease enzyme of about 433 amino-acids and a molecular weight of approximately 45 kd. The first segment is the nucleotide sequence encoding the pro sequence of JP170 protease (that is not a part of the mature protease) and 40 amino acids of the N terminal of the mature JP170 protease. This is followed by a fusion primer segment encoding 8 amino acids (this segment may contain sequence variation due to the degeneration of the primer SF16A767F). The third segment is encoding the approximately 343 amino acid long core. This segment includes the sequence encoding the active site of the protease. This is followed by a fusion primer segment encoding 7 amino acids (this segment may contain variation due to the degeneration of the primer SF16A1802R). The fifth segment is encoding the 35 amino acids of the C terminal of the JP170 protease.

SOE PCR products based on core segments from the strains CDJ120 (SEQ ID NO:3) (the SEQ ID NO of the gene sequence encoding the mature hybrid protease is indicated in brackets) were generated.

The core of the subtilase of the invention may comprise 50-420 amino acid residues, preferably 50-100 amino acid residues, 100-150 amino acid residues, 150-200 amino acid residues 200-250 amino acid residues, 250-300 amino acid residues, 300-350 amino acid residues, 350-400 amino acid residues, 400-420 amino acid residues. Especially preferred is a core segment comprising approximately 343 amino acid residues.

The N terminal end of the core segment is located in one of positions 1-10, 10-20, 20-30, 30-40, 40-50, 50-60 or 60-70 of the subtilase of SEQ ID NO:4. The C terminal end of the core segment is located in one of positions 70-80, 80-90, 90-100, 100-150, 150-200, 200-250, 250-300, 300-320, 320-340, 340-360, 360-380, 380-400, 400-420 of the subtilase of SEQ ID NO:4.

In a preferred embodiment the core of the subtilase of the invention comprises the amino acids in position 49-392 of the hybrid JP170/CDJ120 (SEQ ID NO:4).

The core sequence preferably has 99.2% identity with the amino acids in position 49-392 of SEQ ID NO:4. More preferably the core sequence has 99.3% identity, 99.5% identity, 99.7% identity or 99.9% identity with SEQ ID NO:4.

The corresponding nucleotides encoding the core segment can be seen in SEQ ID NO:3. In a preferred embodiment the core of the subtilase of the invention is encoded by the nucleotides in position 145-1177 of the hybrid JP170/CDJ120 (SEQ ID NO:3).

The N and C terminals of the hybrids of the present invention could equally well be selected from other subtilases, such as BLSCAR, BMSAMP, BASBPN or BSSDY of I-S1, BLSAVI, BAALKP, BLSUBL or subtilisin 147 of I-S2, a members of the TY145 like subtilases, or another member of the JP170 like subtilases.

The lengths of the N and C terminal sequences vary from 1 to approximately 150 amino acid residues. Preferably the length of the terminals are 1-20 amino acid residues, 20-40 amino acid residues, 40-60 amino acid residues, 60-80 amino acid residues, 80-100 amino acid residues, 100-120 amino acid residues, 120-150 amino acid residues.

The subtilase hybrids of the invention are preferable produced by use of the fusion primers described in Example 2, but other suitable primers may equally well be used.

Cloning of the Hybrid Protease

The PCR fragment was cloned into plasmid pDG268NeoMCS-PramyQ/PrcryIII/cryIIIAstab/Sav (U.S. Pat. No. 5,955,310) and transformed in *Bacillus subtilis*. Protease positive colonies were selected and the coding sequence of the expressed enzyme from the expression construct was confirmed by DNA sequence analysis.

Cloning and Expression of Full Length Subtilase of the Invention

Inverse PCR

Inverse PCR was performed with specific DNA primers designed to complement the DNA sequence of the core PCR product and chromosomal DNA extracted from the appropriate bacterial strain. Inverse PCR was made on the strains CDJ120. The inverse PCR products were nucleotide sequenced to obtain the region encoding the N and C terminal parts of the mature subtilase gene.

Production of Full Length Subtilase

The subtilase genes were amplified with specific primers with restriction sites in the 5' end of primers that allow gene fusion with the Savinase signal peptide of plasmid pDG268NeoMCS-PramyQ/PrcryIII/cryIIIAstab/Sav (U.S. Pat. No. 5,955,310). Protease positive colonies were selected and the coding sequence of the expressed enzyme from the expression construct was confirmed by DNA sequence analysis.

Subtilases of the Invention

The subtilase of the present invention include the members of the novel subgroup of FIG. 1: CDJ120. According to the identity matrix of FIG. 2 the sequence identity of the closest related prior art subtilase is 98.2%.

Thus, the subtilase of the present invention is at least 98.5% identical with SEQ ID NO:2 or SEQ ID NO:4. In particular said subtilase may be at least 99% or at least 99.5% identical with SEQ ID NO:2 or SEQ ID NO:4.

The subtilase of the present invention is encoded by an isolated nucleic acid sequence, which nucleic acid sequence has at least 91% identity with SEQ ID NO:1 or SEQ ID NO:3. Preferably, said nucleic acid sequence has at least 92%, at least 93%, at least 94%, at least 95%, at least 96%, at least 97%, at least 98%, or at least 99% identity with the nucleic acid sequence shown in SEQ ID NO:1 or SEQ ID NO:3.

Further the isolated nucleic acid sequence encoding a subtilase of the invention hybridizes with a complementary strand of the nucleic acid sequence shown in SEQ ID NO:1 or SEQ ID NO:3 preferably under low stringency conditions, at least under medium stringency conditions, at least under medium/high stringency conditions, at least under high stringency conditions, at least under very high stringency conditions.

Hybridization

Suitable experimental conditions for determining hybridization between a nucleotide probe and a homologous DNA or RNA sequence involves presoaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5×Denhardt's solution (Sambrook et al. 1989), 0.5% SDS and 100 μg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) *Anal. Biochem.* 132:6-13), $^{32}$P-dCTP-labeled (specific activity>1×10$^9$ cpm/μg) probe for 12 hours at ca. 45° C. For various stringency conditions the filter is then washed twice for 30 minutes in 2×SSC, 0.5% SDS and at least 55° C. (low stringency), more preferably at least 60° C. (medium stringency), still more preferably at least 65° C. (medium/high stringency), even more preferably at least 70° C. (high stringency), and even more preferably at least 75° C. (very high stringency).

Variants

Combined Modifications

The present invention also encompasses any of the above mentioned subtilase variants in combination with any other modification to the amino acid sequence thereof. Especially combinations with other modifications known in the art to provide improved properties to the enzyme are envisaged.

Such combinations comprise the positions: 222 (improves oxidation stability), 218 (improves thermal stability), substitutions in the $Ca^{2+}$-binding sites stabilizing the enzyme, e.g. position 76, and many other apparent from the prior art.

In further embodiments a subtilase variant described herein may advantageously be combined with one or more modification(s) in any of the positions:
27, 36, 56, 76, 87, 95, 96, 97, 98, 99, 100, 101, 102, 103, 104, 120, 123, 159, 167, 170, 206, 218, 222, 224, 232, 235, 236, 245, 248, 252 and 274 (BPN' numbering).
Specifically, the following BLSAVI, BLSUBL, BSKSMK, and BAALKP modifications are considered appropriate for combination:
K27R, *36D, S56P, N76D, S87N, G97N, S101G, S103A, V104A, V104I, V104N, V104Y, H120D, N123S, G159D, Y167, R170, Q206E, N218S, M222S, M222A, T224S, A232V, K235L, Q236H, Q245R, N248D, N252K and T274A.
Furthermore variants comprising any of the modifications S101G+V104N, S87N+S101G+V104N, K27R+V104Y+N123S+T274A, N76D+S103A+V104I or N76D+V104A, or other combinations of the modifications K27R, N76D, S101G, S103A, V104N, V104Y, V104I, V104A, N123S, G159D, A232V, Q236H, Q245R, N248D, N252K, T274A in combination with any one or more of the modification(s) mentioned above exhibit improved properties.

A particular interesting variant is a variant, which, in addition to modifications according to the invention, contains the following substitutions:
S101G+S103A+V104I+G159D+A232V+Q236H+Q245R+N248D+N252K.

Moreover, subtilase variants of the main aspect(s) of the invention are preferably combined with one or more modification(s) in any of the positions 129, 131 and 194, preferably as 129K, 131H and 194P modifications, and most preferably as P129K, P131H and A194P modifications. Any of those modification(s) are expected to provide a higher expression level of the subtilase variant in the production thereof.

Methods for Expression and Isolation of Proteins

To express an enzyme of the present invention the above mentioned host cells transformed or transfected with a vector comprising a nucleic acid sequence encoding an enzyme of the present invention are typically cultured in a suitable nutrient medium under conditions permitting the production of the desired molecules, after which these are recovered from the cells, or the culture broth.

The medium used to culture the host cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The media may be prepared using procedures known in the art (see, e.g., references for bacteria and yeast; Bennett, J. W. and LaSure, L., editors, More Gene Manipulations in Fungi, Academic Press, CA, 1991).

If the enzymes of the present invention are secreted into the nutrient medium, they may be recovered directly from the medium. If they are not secreted, they may be recovered from cell lysates. The enzymes of the present invention may be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the enzyme in question.

The enzymes of the invention may be detected using methods known in the art that are specific for these proteins. These detection methods include use of specific antibodies, formation of a product, or disappearance of a substrate. For example, an enzyme assay may be used to determine the activity of the molecule. Procedures for determining various kinds of activity are known in the art.

The enzymes of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J-C Janson and Lars Ryden, editors, VCH Publishers, New York, 1989).

When an expression vector comprising a DNA sequence encoding an enzyme of the present invention is transformed/transfected into a heterologous host cell it is possible to enable heterologous recombinant production of the enzyme. An advantage of using a heterologous host cell is that it is possible to make a highly purified enzyme composition, characterized in being free from homologous impurities, which are often present when a protein or peptide is expressed in a homologous host cell. In this context homologous impurities mean any impurity (e.g. other polypeptides than the enzyme of the invention) which originates from the homologous cell where the enzyme of the invention is originally obtained from.

Detergent Applications

The enzyme of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations, especially for automatic dish washing (ADW).

In a specific aspect, the invention provides a detergent additive comprising the enzyme of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase™, Savinase™ Primase™, Duralase™, Esperase™, and Kannase™ (Novozymes A/S), Maxatase™, Maxacal™ Maxapem™, Properase™, Purafect™, Purafect OxP™, FN2™, and FN3™ (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novozymes A/S).

Amylases: Suitable amylases ($\alpha$ and/or $\beta$) include those of bacterial or fungal origin. Chemically modified or protein engineered mutants are included. Amylases include, for example, $\alpha$-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novozymes A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Celluzyme™, Renozyme® and Carezyme™ (Novozymes A/S), Clazinase™, and Puradax HA™ (Genencor International Inc.), and KAC-500(B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions any enzyme, in particular the enzyme of the invention, may be added in an amount corresponding to 0.01-100 mg of enzyme protein per litre of wash liquor, preferably 0.05-5 mg of enzyme protein per litre of wash liquor, in particular 0.1-1 mg of enzyme protein per litre of wash liquor.

The enzyme of the invention may additionally be incorporated in the detergent formulations disclosed in WO 97/07202 which is hereby incorporated as reference.

Typical powder detergent compositions for automated dishwashing include:

1)

| Nonionic surfactant | 0.4-2.5% |
| --- | --- |
| Sodium metasilicate | 0-20% |
| Sodium disilicate | 3-20% |
| Sodium triphosphate | 20-40% |
| Sodium carbonate | 0-20% |
| Sodium perborate | 2-9% |
| Tetraacetyl ethylene diamine (TAED) | 1-4% |
| Sodium sulphate | 5-33% |
| Enzymes | 0.0001-0.1% |

2)

| Nonionic surfactant (e.g. alcohol ethoxylate) | 1-2% |
| --- | --- |
| Sodium disilicate | 2-30% |
| Sodium carbonate | 10-50% |
| Sodium phosphonate | 0-5% |
| Trisodium citrate dehydrate | 9-30% |
| Nitrilotrisodium acetate (NTA) | 0-20% |
| Sodium perborate monohydrate | 5-10% |
| Tetraacetyl ethylene diamine (TAED) | 1-2% |
| Polyacrylate polymer (e.g. maleic acid/acrylic acid copolymer) | 6-25% |
| Enzymes | 0.0001-0.1% |
| Perfume | 0.1-0.5% |
| Water | 5-10 |

3)

| Nonionic surfactant | 0.5-2.0% |
| --- | --- |
| Sodium disilicate | 25-40% |
| Sodium citrate | 30-55% |
| Sodium carbonate | 0-29% |
| Sodium bicarbonate | 0-20% |
| Sodium perborate monohydrate | 0-15% |
| Tetraacetyl ethylene diamine (TAED) | 0-6% |
| Maleic acid/acrylic acid copolymer | 0-5% |
| Clay | 1-3% |
| Polyamino acids | 0-20% |
| Sodium polyacrylate | 0-8% |
| Enzymes | 0.0001-0.1% |

4)

| Nonionic surfactant | 1-2% |
| --- | --- |
| Zeolite MAP | 15-42% |
| Sodium disilicate | 30-34% |
| Sodium citrate | 0-12% |
| Sodium carbonate | 0-20% |
| Sodium perborate monohydrate | 7-15% |
| Tetraacetyl ethylene diamine (TAED) | 0-3% |
| Polymer | 0-4% |
| Maleic acid/acrylic acid copolymer | 0-5% |
| Organic phosphonate | 0-4% |
| Clay | 1-2% |
| Enzymes | 0.0001-0.1% |
| Sodium sulphate | Balance |

5)

| Nonionic surfactant | 1-7% |
| --- | --- |
| Sodium disilicate | 18-30% |
| Trisodium citrate | 10-24% |
| Sodium carbonate | 12-20% |
| Monopersulphate ($2KHSO_5 \cdot KHSO_4 \cdot K_2SO_4$) | 15-21% |
| Bleach stabilizer | 0.1-2% |
| Maleic acid/acrylic acid copolymer | 0-6% |
| Diethylene triamine pentaacetate, pentasodium salt | 0-2.5% |
| Enzymes | 0.0001-0.1% |
| Sodium sulphate, water | Balance |

Powder and liquid dishwashing compositions with cleaning surfactant system typically include the following ingredients:

6)

| Nonionic surfactant | 0-1.5% |
| --- | --- |
| Octadecyl dimethylamine N-oxide dihydrate | 0-5% |
| 80:20 wt. C18/C16 blend of octadecyl dimethylamine N-oxide dihydrate and hexadecyldimethyl amine N-oxide dihydrate | 0-4% |
| 70:30 wt. C18/C16 blend of octadecyl bis (hydroxyethyl)amine N-oxide anhydrous and hexadecyl bis (hydroxyethyl)amine N-oxide anhydrous | 0-5% |
| $C_{13}$-$C_{15}$ alkyl ethoxysulfate with an average degree of ethoxylation of 3 | 0-10% |
| $C_{12}$-$C_{15}$ alkyl ethoxysulfate with an average degree of ethoxylation of 3 | 0-5% |
| $C_{13}$-$C_{15}$ ethoxylated alcohol with an average degree of ethoxylation of 12 | 0-5% |
| A blend of $C_{12}$-$C_{15}$ ethoxylated alcohols with an average degree of ethoxylation of 9 | 0-6.5% |
| A blend of $C_{13}$-$C_{15}$ ethoxylated alcohols with an average degree of ethoxylation of 30 | 0-4% |

-continued

| | |
|---|---|
| Sodium disilicate | 0-33% |
| Sodium tripolyphosphate | 0-46% |
| Sodium citrate | 0-28% |
| Citric acid | 0-29% |
| Sodium carbonate | 0-20% |
| Sodium perborate monohydrate | 0-11.5% |
| Tetraacetyl ethylene diamine (TAED) | 0-4% |
| Maleic acid/acrylic acid copolymer | 0-7.5% |
| Sodium sulphate | 0-12.5% |
| Enzymes | 0.0001-0.1% |

Non-aqueous liquid automatic dishwashing compositions typically include the following ingredients:

7)

| | |
|---|---|
| Liquid nonionic surfactant (e.g. alcohol ethoxylates) | 2.0-10.0% |
| Alkali metal silicate | 3.0-15.0% |
| Alkali metal phosphate | 20.0-40.0% |
| Liquid carrier selected from higher glycols, polyglycols, polyoxides, glycolethers | 25.0-45.0% |
| Stabilizer (e.g. a partial ester of phosphoric acid and a $C_{16}$-$C_{18}$ alkanol) | 0.5-7.0% |
| Foam suppressor (e.g. silicone) | 0-1.5% |
| Enzymes | 0.0001-0.1% |

8)

| | |
|---|---|
| Liquid nonionic surfactant (e.g. alcohol ethoxylates) | 2.0-10.0% |
| Sodium silicate | 3.0-15.0% |
| Alkali metal carbonate | 7.0-20.0% |
| Sodium citrate | 0.0-1.5% |
| Stabilizing system (e.g. mixtures of finely divided silicone and low molecular weight dialkyl polyglycol ethers) | 0.5-7.0% |
| Low molecule weight polyacrylate polymer | 5.0-15.0% |
| Clay gel thickener (e.g. bentonite) | 0.0-10.0% |
| Hydroxypropyl cellulose polymer | 0.0-0.6% |
| Enzymes | 0.0001-0.1% |
| Liquid carrier selected from higher lycols, polyglycols, polyoxides and glycol ethers | Balance |

Thixotropic liquid automatic dishwashing compositions typically include the following ingredients:

9)

| | |
|---|---|
| $C_{12}$-$C_{14}$ fatty acid | 0-0.5% |
| Block co-polymer surfactant | 1.5-15.0% |
| Sodium citrate | 0-12% |
| Sodium tripolyphosphate | 0-15% |
| Sodium carbonate | 0-8% |
| Aluminium tristearate | 0-0.1% |
| Sodium cumene sulphonate | 0-1.7% |
| Polyacrylate thickener | 1.32-2.5% |
| Sodium polyacrylate | 2.4-6.0% |
| Boric acid | 0-4.0% |
| Sodium formate | 0-0.45% |
| Calcium formate | 0-0.2% |
| Sodium n-decydiphenyl oxide disulphonate | 0-4.0% |
| Monoethanol amine (MEA) | 0-1.86% |
| Sodium hydroxide (50%) | 1.9-9.3% |
| 1,2-Propanediol | 0-9.4% |
| Enzymes | 0.0001-0.1% |
| Suds suppressor, dye, perfumes, water | Balance |

Liquid automatic dishwashing compositions typically include the following ingredients:

10)

| | |
|---|---|
| Alcohol ethoxylate | 0-20% |
| Fatty acid ester sulphonate | 0-30% |
| Sodium dodecyl sulphate | 0-20% |
| Alkyl polyglycoside | 0-21% |
| Oleic acid | 0-10% |
| Sodium disilicate monohydrate | 18-33% |
| Sodium citrate dihydrate | 18-33% |
| Sodium stearate | 0-2.5% |
| Sodium perborate monohydrate | 0-13% |
| Tetraacetyl ethylene diamine (TAED) | 0-8% |
| Maleic acid/acrylic acid copolymer | 4-8% |
| Enzymes | 0.0001-0.1% |

Liquid automatic dishwashing compositions containing protected bleach particles typically include the following ingredients:

11)

| | |
|---|---|
| Sodium silicate | 5-10% |
| Tetrapotassium pyrophosphate | 15-25% |
| Sodium triphosphate | 0-2% |
| Potassium carbonate | 4-8% |
| Protected bleach particles, e.g. chlorine | 5-10% |
| Polymeric thickener | 0.7-1.5% |
| Potassium hydroxide | 0-2% |
| Enzymes | 0.0001-0.1% |
| Water | Balance |

12) Automatic dishwashing compositions as described in 1), 2), 3), 4), 6) and 10), wherein perborate is replaced by percarbonate.

13) Automatic dishwashing compositions as described in 1)-6) which additionally contain a manganese catalyst. The manganese catalyst may, e.g., be one of the compounds described in "Efficient manganese catalysts for low-temperature bleaching", Nature 369, 1994, pp. 637-639.

Materials and Methods

Method for Producing a Subtilase Variant

The present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

When an expression vector comprising a DNA sequence encoding the enzyme is transformed into a heterologous host cell it is possible to enable heterologous recombinant production of the enzyme of the invention. Thereby it is possible to make a highly purified subtilase composition, characterized in being free from homologous impurities.

The medium used to culture the transformed host cells may be any conventional medium suitable for growing the host cells in question. The expressed subtilase may conveniently be secreted into the culture medium and may be recovered there-from by well-known procedures including separating the cells from the medium by centrifugation or filtration, precipitating proteinaceous components of the medium by means of a salt such as ammonium sulfate, followed by chromatographic procedures such as ion exchange chromatography, affinity chromatography, or the like.

Example 1

PCR Screening

The core part of protease gene was amplified in a PCR reaction that included 50 U/ml of Ampli-taq™ DNA polymerase (Perkin Elmer) 10× Amplitaq buffer (final concentration of $MgCl_2$ is 1.5 mM) 0.2 mM of each of the dNTPs (dATP, dCTP, dTTP and dGTP) 0.2 pmol/μl of the primers SF16A767F (CNATGCATGAAGCNTTCCGCGG, SEQ ID NO:5) ("N" is degeneration introduced by insertion of inosine)) and SF16A1802R (CNACGTTGTTNCNGC-CATCCC, SEQ ID NO:6) and 1 μl template DNA. Template DNA was recovered from the various *Bacillus* strains using HighPure™ PCR template preparation kit (Boehringer Mannheim art. 1796828) as recommended by the manufacturer for DNA recovery from bacteria. The quality of the isolated template was evaluated by agarose gel electrophoresis. If a high molecular weight band was present the quality was accepted. PCR was run in the following protocol: 94° C., 2 minutes 40 cycles of [94° C. for 30 seconds, 52° C. for 30 seconds, 68° C. for 1 minute] completed with 68° C. for 10 minutes. PCR products were analysed on a 1% agarose gel in TAE buffer stained with Ethidium bromide to confirm a single band of app. 1050 nucleotides. The PCR product was recovered by using Qiagen™ PCR purification kit as recommended by the manufacturer. The nucleotide sequences were determined by sequencing on an ABI PRISM™ DNA sequencer (Perkin Elmer). A PCR product of CDJ120 was determined. The nucleotide sequences were translated to amino acid sequences, and the diversity analysed by comparative peptide sequence analysis. As can be seen in FIG. 1 the diversity by far exceeded that of the prior art.

Example 2

Production of Subtilase Hybrids

Expression of Hybrid Proteases, PCR Amplification

In order to produce an active subtilase based on the nucleotide sequence information of the partial sequencing of Example 1, the core PCR product was fused to the N and C terminal parts of the JP170 protease gene in a SOE PCR (SOE: Splicing by Overlapping Extension) reaction as described above. In the SOE PCR reaction a fusion of three PCR products are produced. The three PCR products are:
1) The N terminal part of JP170 protease gene. This PCR product is obtained by PCR using the primers

```
                                      (SEQ ID NO: 12)
PEP192 5'-CCGCGGAATGCTTCATGCATCG-3'
and
                                      (SEQ ID NO: 13)
PEP200 5'-GTTCATCGATCTTCTACTATTGGGGCGAAC-3'
``` and 1 μl template DNA. Template DNA was recovered from the various *Bacillus* strains using HighPure™ PCR template preparation kit (Boehringer Mannheim art. 1796828) as recommended by the manufacturer for DNA recovery from bacteria. The quality of the isolated template was evaluated by agarose gel electrophoresis. If a high molecular weight band was present the quality was accepted. PCR was run in the following protocol: 94° C., 2 minutes 40 cycles of [94° C. for 30 seconds, 52° C. for 30 seconds, 68° C. for 1 minute] completed with 68° C. for 10 minutes. PCR products were analysed on a 1% agarose gel in TAE buffer stained with Ethidium bromide to confirm a single band of app. 700 nucleotides.

2) The C terminal part of JP170 protease gene. This PCR product is obtained by PCR using the primers

```
                                      (SEQ ID NO: 14)
PEP193 5'-GGGATGGCAGAAACAACGTGG-3'
and
                                      (SEQ ID NO: 15)
PEP201 5'-TTAAACGCGTTTAATGTACAATCGCTAAAGAAAAG-3'
``` and 1 μl template DNA. Template DNA was recovered from the various *Bacillus* strains using HighPure™ PCR template preparation kit (Boehringer Mannheim art. 1796828) as recommended by the manufacturer for DNA recovery from bacteria. The quality of the isolated template was evaluated by agarose gel electrophoresis. If a high molecular weight band was present the quality was accepted. PCR was run in the following protocol: 94° C., 2 minutes 40 cycles of [94° C. for 30 seconds, 52° C. for 30 seconds, 68° C. for 1 minute] completed with 68° C. for 10 minutes. PCR products were analysed on a 1% agarose gel in TAE buffer stained with Ethidium bromide to confirm a single band of app. 370 nucleotides.

3) The core PCR product described in Example 1.

In the SOE PCR reaction the three PCR products are mixed and a fused product is amplified in a standard PCR protocol using the primers PEP200 and PEP201 and 1 μl template DNA. Template DNA is a mixture of the three PCR products described above (1-3). These PCR products may be recovered using Qiaquick™ spin columns as recommended (Qiagen, Germany). The quality of the isolated template was evaluated by agarose gel electrophoresis. PCR was run in the following protocol: 94° C., 2 minutes 40 cycles of [94° C. for 30 seconds, 52° C. for 30 seconds, 68° C. for 1 minute] completed with 68° C. for 10 minutes. PCR products were analysed on a 1% agarose gel in TAE buffer stained with Ethidium bromide to confirm a single band of app. 1850 nucleotides.

The digested and purified PCR fragment was ligated to the Cla I and Mlu I digested plasmid pDG268NeoMCS-PramyQ/PrcryIII/cryIIIAstab/Sav (U.S. Pat. No. 5,955,310). The ligation mixture was used for transformation into *E. coli* TOP10F' (Invitrogen BV, The Netherlands) and several colonies were selected for miniprep (QIAprep® spin, QIAGEN GmbH, Germany). The purified plasmids were checked for insert before transformation into a strain of *Bacillus subtilis* derived from *B. subtilis* DN 1885 with disrupted apr, npr and pel genes (Diderichsen et al (1990), J. Bacteriol., 172, 4315-4321). The disruption was performed essentially as described in "*Bacillus subtilis* and other Gram-Positive Bacteria," American Society for Microbiology, p. 618, eds. A. L. Sonenshein, J. A. Hoch and Richard Losick (1993). Transformed cells were plated on 1% skim milk LB-PG agar plates, supplemented with 6 μg/ml chloramphenicol. The plated cells were incubated over night at 37° C. and protease containing colonies were identified by a surrounding clearing zone. Protease positive colonies were selected and the coding sequence of the expressed enzyme from the expression construct was confirmed by DNA sequence analysis.

Example 3

Production of Full Length Subtilases

Inverse PCR

Three digestions of the chromosomal DNA of the strains CDJ120 were made using the restriction enzymes xho1, BamH1 and Pst1. Upon digestion the DNA was separated from the restriction enzymes using Qiaquick™ PCR purification kit (art. 28106, Qiagen, Germany). The digestions were religated and subjected to a PCR reaction using primers (PCR primers SEQ ID NO:7-8) designed to recognise the sequence of the PCR product already obtained. The following PCR protocols were applied: 94° C. 2 min 30 cycles of [94° C. for 15 s, 52° C. for 30 s, 72° C. for 2 min] 72° C. 20 min. Using same PCR amount of primer polymerase and buffer as above. Alternatively a protocol with 94° C. 2 min 30 cycles of [94° C. for 15 s, 52° C. for 30 s, 68° C. for 3 min] 68° C. 20 min. and replacing Amplitaq® and Amplitaq® buffer with Long-template Taq Polymerase™ (Boehringer Mannheim) with the buffer supplied with the polymerase. The PCR reactions were analysed on 0.8% agarose gels stained with ethidium bromide. All PCR fragments were recovered and the nucleotide sequence was determined by using specific oligo primers different from those used in the PCR reaction (Sequencing primers SEQ ID NO:9-11). In some cases the first primer did not give sufficient nucleotide sequence information to characterise the entire open reading frame of the protease gene. In these cases new primers were applied either by using the sequence information obtained with the initial inverse PCR sequencing primer, or by going back to the initial PCR fragment and defining a new primer sequence.

The following primers were used for obtaining the inverse PCR and sequencing:
PCR Primers

```
CDJ120 PCR Forward:
CCGAACGGAAACCAAGGATGGG      (SEQ ID NO: 7)

CDJ120 PCR Reverse:
GGAGCCGTTTCCTAATACAGAG      (SEQ ID NO: 8)
```

Sequencing Primers

```
CDJ120 Forward Sequencing
TTGGACCTTGTCATTACCGC        (SEQ ID NO: 9)

CDJ120 Reverse Sequencing1
AGACCTCCAAGTCCTCCACC        (SEQ ID NO: 10)

CDJ120 Reverse Sequencing2
CATTGCTTGCTGCGTATTGG        (SEQ ID NO: 11)
```

The gene sequence encoding the mature part of the protease gene of strain CDJ120 is shown in SEQ ID NO:1.
PCR Amplification In order to produce an active subtilase based on the nucleotide sequence information of the 1305 nucleotide gene segment encoding the full length mature CDJ120 subtilase (SEQ ID NO:1), a gene fusion was made to the DNA encoding the pro sequence of the JP170 protease by SOE PCR.

Two PCR fragments were amplified:
1) The nucleotide sequence encoding the full length mature CDJ120 subtilase was amplified with primers CDJ120 Mlu1_R TTAAACGCGTTTAGTTTACAATTGCCAACG (SEQ ID NO:16) and CDJ120 SOEF AATGANGTGGC-CCGNGGNATTG (SEQ ID NO:17, N is inosine) using CDJ120 chromosomal DNA (this gene segment is deposited as plasmid DNA contained in DSM16721).

2) The pro sequence of the JP170 subtilase gene was amplified using primers JP170_CDJ120_SOE_R CAATGC-CACGGGCCACGTCATT (SEQ ID NO:18). PEP200 5'-GT-TCATCGATCTTCTACTATTGGGGCGAAC-3' (SEQ ID NO:13) and JP170 chromosomal DNA as template. Template DNA was recovered from the various *Bacillus* strains using HighPure™ PCR template preparation kit (Boehringer Mannheim art. 1796828) as recommended by the manufacturer for DNA recovery from bacteria. The quality of the isolated template was evaluated by agarose gel electrophoresis. If a high molecular weight band was present the quality was accepted.

Both PCR were run in the following protocol: 94° C., 2 minutes 40 cycles of [94° C. for 30 seconds, 52° C. for 30 seconds, 68° C. for 1 minute] completed with 68° C. for 10 minutes. PCR products were analysed on a 1% agarose gel in TAE buffer stained with Ethidium bromide to confirm a single band of app. 700 nucleotides.

In the subsequent SOE PCR reaction a fusion of two PCR products were produced. PCR was run in the following protocol: 94° C., 2 minutes 40 cycles of [94° C. for 30 seconds, 52° C. for 30 seconds, 68° C. for 1 minute] completed with 68° C. for 10 minutes. PCR products were analysed on a 1% agarose gel in TAE buffer stained with Ethidium bromide to confirm a single band of app. 1850 nucleotides.

The digested and purified PCR fragment was ligated to the Cla I and Mlu I digested plasmid pDG268NeoMCS-PramyQ/PrcryIII/cryIIIAstab/Sav (U.S. Pat. No. 5,955,310).

The ligation mixture was used for transformation into *E. coli* TOP10F' (Invitrogen BV, The Netherlands) and several colonies were selected for miniprep (QIAprep® spin, QIAGEN GmbH, Germany). The purified plasmids were checked for insert before transformation into a strain of *Bacillus subtilis* derived from *B. subtilis* DN 1885 with disrupted apr, npr and pel genes (Diderichsen et al (1990), J. Bacteriol., 172, 4315-4321). The disruption was performed essentially as described in "*Bacillus subtilis* and other Gram-Positive Bacteria," American Society for Microbiology, p. 618, eds. A. L. Sonenshein, J. A. Hoch and Richard Losick (1993). Transformed cells were plated on 1% skim milk LB-PG agar plates, supplemented with 6 μg/ml chloramphenicol. The plated cells were incubated over night at 37° C. and protease containing colonies were identified by a surrounding clearing zone. Protease positive colonies were selected and the coding sequence of the expressed enzyme from the expression construct was confirmed by DNA sequence analysis.

Example 4

Purification and Characterisation

Purification

This procedure relates to purification of a 2 liter scale fermentation for the production of the subtilases of the invention in a *Bacillus* host cell.

Approximately 1.6 liters of fermentation broth are centrifuged at 5000 rpm for 35 minutes in 1 liter beakers. The supernatants are adjusted to pH 6.5 using 10% acetic acid and filtered on Seitz Supra® S100 filter plates.

The filtrates are concentrated to approximately 400 ml using an Amicon® CH2A UF unit equipped with an Amicon® S1Y10 UF cartridge. The UF concentrate is centrifuged and filtered prior to absorption at room temperature on a Bacitracin affinity column at pH 7. The protease is eluted from the Bacitracin column at room temperature using 25%

2-propanol and 1 M sodium chloride in a buffer solution with 0.01 dimethylglutaric acid, 0.1 M boric acid and 0.002 M calcium chloride adjusted to pH 7.

The fractions with protease activity from the Bacitracin purification step are combined and applied to a 750 ml Sephadex® G25 column (5 cm dia.) equilibrated with a buffer containing 0.01 dimethylglutaric acid, 0.2 M boric acid and 0.002 m calcium chloride adjusted to pH 6.5.

Fractions with proteolytic activity from the Sephadex® G25 column are combined and applied to a 150 ml CM Sepharose® CL 6B cation exchange column (5 cm dia.) equilibrated with a buffer containing 0.01 M dimethylglutaric acid, 0.2 M boric acid, and 0.002 M calcium chloride adjusted to pH 6.5.

The protease is eluted using a linear gradient of 0-0.1 M sodium chloride in 2 litres of the same buffer.

In a final purification step subtilase containing fractions from the CM Sepharose® column are combined and concentrated in an Amicon® ultrafiltration cell equipped with a GR81PP membrane (from the Danish Sugar Factories Inc.).

Example 5

Stability of Subtilases

The stability of the produced subtilases was evaluated in a standard Western European dishwashing tablet detergent without other enzymes than the experimentally added subtilases. The stability of the subtilases is determined as the residual proteolytic activity after incubation of the subtilase in a detergent.

The formulation of a standard Western European Tablet detergent is defined as

| Component | Percentage |
|---|---|
| Non ionic surfactants | 0-10% |
| Foam regulators | 1-10% |
| Bleach (per-carbonate or per-borate) | 5-15% |
| Bleach activators (e.g. TAED) | 1-5% |
| Builders (e.g. carbonate, phosphate, tri-phosphate, Zeolite) | 50-75% |
| Polymers | 0-15% |
| Perfume, dye etc. | <1% |
| Water and fillers (e.g. sodium sulphate) | Balance |

Assay for Proteolytic Activity

The proteolytic activity was determined with casein as substrate. One Casein Protease Unit (CPU) is defined as the amount of protease liberating about 1 µM of primary amino groups (determined by comparison with a serine standard) per minute under standard conditions, i.e., incubation for about 30 minutes at about 25° C. at pH 9.5.

The proteolytic activity may also be determined by measuring the specific hydrolysis of succinyl-Ala-Ala-Pro-Leu-p-nitroanilide by said protease. The substrate is initially dissolved in for example, DMSO (Dimethyl Sulfoxide) and then diluted about 50 fold in about 0.035 M borate buffer, about pH 9.45. All protease samples may be diluted about 5-10 fold by the same borate buffer. Equal volumes of the substrate solution and sample are mixed in a well of an ELISA reader plate and read at about 405 nm at 25° C. All sample activities and concentrations are normalized to the standard protease solution activity and concentration, respectively.

A typical Western European tablet detergent for automated dishwashing was dissolved (5.5 g/L) in 9° dH water at ambient temperature maximum 30 minutes prior to start of analyses. Samples of subtilases were diluted to a concentration of 2-4 CPU/ml in Britten Robinson buffer (Britten Robinson buffer is: 40 mM Phosphate, 40 mM Acetate and 40 mM Borate) pH9.5. For the analyses every sample was divided and tested under two conditions: For the control the subtilase was diluted 1:9 in Britten Robinson buffer pH9.5 to a final volume of 1 ml. This sample was analysed immediately after dilution. For the detergent stability the subtilase sample was diluted 1:9 in detergent solution (detergent concentration in the stability test is 5 g/L) these samples were incubated at 55° C. for 30 minutes prior to analysis by addition of casein substrate.

The assay was started by addition of 2 volumes of casein substrate (casein substrate was 2 g of casein (Merck, Hammerstein grade) in 100 ml of Britten Robinson buffer pH 9.5, pH was re-adjusted to 9.5 when the casein is in solution). Samples are kept isothermic at 25° C. for 30 minutes. The reaction was stopped by addition of 5 ml TCA solution (TCA solution is 89.46 g of Tri-chloric acid, 149.48 g of Sodium acetate-tri-hydrate and 94.5 ml of glacial acetic acid in 2.5 L of deionised water). The samples are incubated at ambient temperature for at least 20 minutes and filtered through Whatman® paper filter no. 42.

400 µl of filtrate is mixed with 3 ml OPA reagent (OPA reagent is composed of: 3.812 g of borax, 0.08% EtOH, 0.2% DTT and 80 mg of o-phthal-dialdehyd in 100 ml water). Absorption at 340 nM is measured and CPU is calculated from the concentration of free amines on a standard of a solution of 0.01% L-serine (Merck art. 7769).

Enzymatic proteolysis of reference proteases in the typical Western European tablet detergent:

| | CPU/L | | |
|---|---|---|---|
| Protease | Control | Detergent | % activity |
| Alcalase | 250 | 31 | 13% |
| Esperase | 220 | 116 | 53% |
| Savinase | 538 | 21 | 4% |
| Everlase16L | 2383 | 86 | 4% |
| Ovozyme | 2848 | 44 | 2% |
| BLAP-S | 36 | 1 | 3% |
| JP170 | 754 | 370 | 49% |

Enzymatic proteolysis of cloned hybrid proteases of the invention in the typical Western European tablet detergent. The reference is JP170:

| | CPU/l | | |
|---|---|---|---|
| Hybrid | Control | Detergent | % activity |
| JP170 | 67 | 36 | 53% |
| JP170 | 66 | 38 | 57% |
| CDJ120-1 | 44 | 34 | 77% |
| CDJ120-1 | 46 | 38 | 83% |

As can be seen from the results the subtilases of the invention exhibit improved stability in a detergent as compared to the prior art.

The invention claimed is:

1. An isolated subtilase which comprises an amino acid sequence having a modification in up to four positions of SEQ ID NO: 4, wherein the subtilase has protease activity.

2. The isolated subtilase of claim 1, which comprises an amino acid sequence having a modification in four positions of SEQ ID NO: 4.

3. The isolated subtilase of claim 1, which comprises an amino acid sequence having a modification in three positions of SEQ ID NO: 4.

4. The isolated subtilase of claim 1, which comprises an amino acid sequence having a modification in two positions of SEQ ID NO: 4.

5. The isolated subtilase of claim 1, which comprises an amino acid sequence having a modification in one position of SEQ ID NO: 4.

6. The isolated subtilase of claim 1, which comprises the sequence of SEQ ID NO: 4.

7. An isolated subtilase, which comprises an amino acid sequence from position 49 to position 392 of SEQ ID NO: 4, wherein the subtilase has protease activity.

8. An isolated nucleic acid sequence encoding the subtilase of claim 1.

9. The nucleic acid sequence of claim 8, which comprises SEQ ID NO: 3.

10. A nucleic acid construct comprising the nucleic acid sequence of claim 8 operably linked to one or more control sequences capable of directing the expression of the polypeptide in a suitable expression host.

11. A recombinant expression vector comprising the nucleic acid construct of claim 10, a promoter, and transcriptional and translational stop signals.

12. A recombinant host cell comprising the nucleic acid construct of claim 10.

13. A method for producing a subtilase, comprising
   (a) cultivating the host cell of claim 12 under conditions conducive to expression of the subtilase; and
   (b) recovering the subtilase.

14. A detergent composition comprising the subtilase of claim 1 and a surfactant.

15. A detergent composition comprising the subtilase of claim 2 and a surfactant.

16. A detergent composition comprising the subtilase of claim 3 and a surfactant.

17. A detergent composition comprising the subtilase of claim 4 and a surfactant.

18. A detergent composition comprising the subtilase of claim 5 and a surfactant.

19. A detergent composition comprising the subtilase of claim 6 and a surfactant.

20. A detergent composition comprising the subtilase of claim 7 and a surfactant.

* * * * *

SEQUENCE LISTING

<160> NUMBER OF SEQ ID NOS: 18

<210> SEQ ID NO 1
<211> LENGTH: 1305
<212> TYPE: DNA
<213> ORGANISM: Bacillus
<220> FEATURE:
<221> NAME/KEY: CDS
<222> LOCATION: (1)..(1305)

<400> SEQUENCE: 1

| aat | gat | gtg | gcc | cga | gga | att | gtc | aag | gcg | gac | gtg | gct | cag | agc | agc | 48 |
|---|---|---|---|---|---|---|---|---|---|---|---|---|---|---|---|---|
| Asn | Asp | Val | Ala | Arg | Gly | Ile | Val | Lys | Ala | Asp | Val | Ala | Gln | Ser | Ser | |
| 1 | | | | 5 | | | | | 10 | | | | | 15 | | |

| tac | ggt | ttg | tat | gga | caa | ggg | cag | att | gta | gct | gta | gcc | gac | acg | ggg | 96 |
|---|---|---|---|---|---|---|---|---|---|---|---|---|---|---|---|---|
| Tyr | Gly | Leu | Tyr | Gly | Gln | Gly | Gln | Ile | Val | Ala | Val | Ala | Asp | Thr | Gly | |
| | | | 20 | | | | | 25 | | | | | 30 | | | |

| ctt | gat | aca | gga | aaa | aac | gac | agt | acg | atg | cat | gaa | gcc | ttc | cga | ggg | 144 |
|---|---|---|---|---|---|---|---|---|---|---|---|---|---|---|---|---|
| Leu | Asp | Thr | Gly | Lys | Asn | Asp | Ser | Thr | Met | His | Glu | Ala | Phe | Arg | Gly | |
| | | | 35 | | | | | 40 | | | | | 45 | | | |

| aaa | att | acg | gca | tta | tat | gca | cta | ggt | cgc | act | aat | aat | gcc | aat | gat | 192 |
|---|---|---|---|---|---|---|---|---|---|---|---|---|---|---|---|---|
| Lys | Ile | Thr | Ala | Leu | Tyr | Ala | Leu | Gly | Arg | Thr | Asn | Asn | Ala | Asn | Asp | |
| 50 | | | | | 55 | | | | | 60 | | | | | | |

| aca | cac | ggt | cat | ggt | acg | cat | gtg | gcg | ggc | tct | gta | tta | gga | aac | ggc | 240 |
|---|---|---|---|---|---|---|---|---|---|---|---|---|---|---|---|---|
| Thr | His | Gly | His | Gly | Thr | His | Val | Ala | Gly | Ser | Val | Leu | Gly | Asn | Gly | |
| 65 | | | | 70 | | | | | 75 | | | | | 80 | | |

| tcc | act | aat | aaa | gga | atg | gca | ccg | cag | gcg | aat | ctt | gtc | ttc | caa | tct | 288 |
|---|---|---|---|---|---|---|---|---|---|---|---|---|---|---|---|---|
| Ser | Thr | Asn | Lys | Gly | Met | Ala | Pro | Gln | Ala | Asn | Leu | Val | Phe | Gln | Ser | |
| | | | 85 | | | | | 90 | | | | | 95 | | | |

| atc | atg | gat | agc | ggt | gga | gga | ctt | gga | ggt | cta | cct | tcg | aat | ctg | caa | 336 |
|---|---|---|---|---|---|---|---|---|---|---|---|---|---|---|---|---|
| Ile | Met | Asp | Ser | Gly | Gly | Gly | Leu | Gly | Gly | Leu | Pro | Ser | Asn | Leu | Gln | |
| | | | 100 | | | | | 105 | | | | | 110 | | | |

| acc | tta | ttc | agc | caa | gca | tac | agt | gca | ggt | gcc | aga | att | cat | aca | aac | 384 |
|---|---|---|---|---|---|---|---|---|---|---|---|---|---|---|---|---|
| Thr | Leu | Phe | Ser | Gln | Ala | Tyr | Ser | Ala | Gly | Ala | Arg | Ile | His | Thr | Asn | |
| | | 115 | | | | | 120 | | | | | 125 | | | | |

| tcc | tgg | gaa | gca | gcg | gta | aat | ggg | gct | tac | acg | aca | gat | tca | agg | aat | 432 |
|---|---|---|---|---|---|---|---|---|---|---|---|---|---|---|---|---|
| Ser | Trp | Glu | Ala | Ala | Val | Asn | Gly | Ala | Tyr | Thr | Thr | Asp | Ser | Arg | Asn | |
| | 130 | | | | | 135 | | | | | 140 | | | | | |

| gtg | gat | gac | tat | gta | cga | aaa | aat | gat | atg | acg | att | ctt | ttc | gct | gcc | 480 |
|---|---|---|---|---|---|---|---|---|---|---|---|---|---|---|---|---|
| Val | Asp | Asp | Tyr | Val | Arg | Lys | Asn | Asp | Met | Thr | Ile | Leu | Phe | Ala | Ala | |
| 145 | | | | | 150 | | | | | 155 | | | | | 160 | |

| gga | aat | gaa | gga | ccg | aac | ggc | gga | acc | atc | agt | gca | cca | ggt | aca | gct | 528 |
|---|---|---|---|---|---|---|---|---|---|---|---|---|---|---|---|---|
| Gly | Asn | Glu | Gly | Pro | Asn | Gly | Gly | Thr | Ile | Ser | Ala | Pro | Gly | Thr | Ala | |
| | | | | 165 | | | | | 170 | | | | | 175 | | |

| aaa | aat | gcc | ata | aca | gtc | ggg | gct | acg | gaa | aac | ctc | cgt | cca | agc | ttc | 576 |
|---|---|---|---|---|---|---|---|---|---|---|---|---|---|---|---|---|
| Lys | Asn | Ala | Ile | Thr | Val | Gly | Ala | Thr | Glu | Asn | Leu | Arg | Pro | Ser | Phe | |
| | | | 180 | | | | | 185 | | | | | 190 | | | |

| ggg | tcc | tat | gcg | gat | aac | atc | aac | cat | gtg | gca | cag | ttt | tct | tca | cgc | 624 |
|---|---|---|---|---|---|---|---|---|---|---|---|---|---|---|---|---|
| Gly | Ser | Tyr | Ala | Asp | Asn | Ile | Asn | His | Val | Ala | Gln | Phe | Ser | Ser | Arg | |
| | | 195 | | | | | 200 | | | | | 205 | | | | |

| gga | cct | aca | aag | gat | gga | cga | atc | aag | ccg | gac | gtc | atg | gct | ccg | gga | 672 |
|---|---|---|---|---|---|---|---|---|---|---|---|---|---|---|---|---|
| Gly | Pro | Thr | Lys | Asp | Gly | Arg | Ile | Lys | Pro | Asp | Val | Met | Ala | Pro | Gly | |
| | 210 | | | | | 215 | | | | | 220 | | | | | |

| acg | ttc | att | tta | tca | gca | aga | tcc | tct | ctt | gca | ccg | gat | tcg | tca | ttc | 720 |
|---|---|---|---|---|---|---|---|---|---|---|---|---|---|---|---|---|
| Thr | Phe | Ile | Leu | Ser | Ala | Arg | Ser | Ser | Leu | Ala | Pro | Asp | Ser | Ser | Phe | |
| 225 | | | | | 230 | | | | | 235 | | | | | 240 | |

| tgg | gcg | aac | cat | gat | agc | aaa | tat | gct | tat | atg | ggt | gga | acg | tcc | atg | 768 |
|---|---|---|---|---|---|---|---|---|---|---|---|---|---|---|---|---|
| Trp | Ala | Asn | His | Asp | Ser | Lys | Tyr | Ala | Tyr | Met | Gly | Gly | Thr | Ser | Met | |
| | | | | 245 | | | | | 250 | | | | | 255 | | |

| gcc | acg | cca | att | gtt | gca | gga | aac | gtg | gca | cag | ctt | cgt | gag | cat | ttt | 816 |

-continued

```
                Ala Thr Pro Ile Val Ala Gly Asn Val Ala Gln Leu Arg Glu His Phe
                                260                 265                 270 gtg aaa aat aga ggc atc aca cca aag cca tct tta tta aaa gcg gca         864
Val Lys Asn Arg Gly Ile Thr Pro Lys Pro Ser Leu Leu Lys Ala Ala
        275                 280                 285 ctg att gct ggt gcg gct gac atc ggg ctt ggc tac ccg aac gga aac         912
Leu Ile Ala Gly Ala Ala Asp Ile Gly Leu Gly Tyr Pro Asn Gly Asn
    290                 295                 300 caa gga tgg ggc cga gtg aca ttg gat aaa tcg ctg aac gtt gcc tat         960
Gln Gly Trp Gly Arg Val Thr Leu Asp Lys Ser Leu Asn Val Ala Tyr
305                 310                 315                 320 gtg aac gaa tct agt tct cta tca act agt caa aaa gcg aca tac tcg        1008
Val Asn Glu Ser Ser Ser Leu Ser Thr Ser Gln Lys Ala Thr Tyr Ser
                325                 330                 335 ttt aca gct act gcc ggc aag ccg ctg aag atc tcc ctg gta tgg tct        1056
Phe Thr Ala Thr Ala Gly Lys Pro Leu Lys Ile Ser Leu Val Trp Ser
            340                 345                 350 gat gca cca gct agc aca act gct tcc gta acg ctc gtc aat gat ttg        1104
Asp Ala Pro Ala Ser Thr Thr Ala Ser Val Thr Leu Val Asn Asp Leu
        355                 360                 365 gac ctt gtc att acc gct cca aat ggc aca caa tat gtt gga aat gac        1152
Asp Leu Val Ile Thr Ala Pro Asn Gly Thr Gln Tyr Val Gly Asn Asp
    370                 375                 380 ttt tct gct cca tac aat aat aac tgg gat ggc cgc aat aac gtg gaa        1200
Phe Ser Ala Pro Tyr Asn Asn Asn Trp Asp Gly Arg Asn Asn Val Glu
385                 390                 395                 400 aat gta ttt atc tcc gcg cca caa agc ggg acg tat act gta gag gtt        1248
Asn Val Phe Ile Ser Ala Pro Gln Ser Gly Thr Tyr Thr Val Glu Val
                405                 410                 415 caa gca tat aac gta ccg gtt gga cca cag aac ttc tcg ttg gca att        1296
Gln Ala Tyr Asn Val Pro Val Gly Pro Gln Asn Phe Ser Leu Ala Ile
            420                 425                 430 gta aac taa                                                             1305
Val Asn <210> SEQ ID NO 2
<211> LENGTH: 434
<212> TYPE: PRT
<213> ORGANISM: Bacillus

<400> SEQUENCE: 2

Asn Asp Val Ala Arg Gly Ile Val Lys Ala Asp Val Ala Gln Ser Ser
1               5                   10                  15

Tyr Gly Leu Tyr Gly Gln Gly Gln Ile Val Ala Val Ala Asp Thr Gly
            20                  25                  30

Leu Asp Thr Gly Lys Asn Asp Ser Thr Met His Glu Ala Phe Arg Gly
        35                  40                  45

Lys Ile Thr Ala Leu Tyr Ala Leu Gly Arg Thr Asn Asn Ala Asn Asp
    50                  55                  60

Thr His Gly His Gly Thr His Val Ala Gly Ser Val Leu Gly Asn Gly
65                  70                  75                  80

Ser Thr Asn Lys Gly Met Ala Pro Gln Ala Asn Leu Val Phe Gln Ser
                85                  90                  95

Ile Met Asp Ser Gly Gly Gly Leu Gly Gly Leu Pro Ser Asn Leu Gln
            100                 105                 110

Thr Leu Phe Ser Gln Ala Tyr Ser Ala Gly Ala Arg Ile His Thr Asn
        115                 120                 125

Ser Trp Glu Ala Ala Val Asn Gly Ala Tyr Thr Thr Asp Ser Arg Asn
    130                 135                 140
```

```
Val Asp Asp Tyr Val Arg Lys Asn Asp Met Thr Ile Leu Phe Ala Ala
145                 150                 155                 160

Gly Asn Glu Gly Pro Asn Gly Thr Ile Ser Ala Pro Gly Thr Ala
            165                 170                 175

Lys Asn Ala Ile Thr Val Gly Ala Thr Glu Asn Leu Arg Pro Ser Phe
            180                 185                 190

Gly Ser Tyr Ala Asp Asn Ile Asn His Val Ala Gln Phe Ser Ser Arg
        195                 200                 205

Gly Pro Thr Lys Asp Gly Arg Ile Lys Pro Asp Val Met Ala Pro Gly
        210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
            245                 250                 255

Ala Thr Pro Ile Val Ala Gly Asn Val Ala Gln Leu Arg Glu His Phe
            260                 265                 270

Val Lys Asn Arg Gly Ile Thr Pro Lys Pro Ser Leu Leu Lys Ala Ala
        275                 280                 285

Leu Ile Ala Gly Ala Ala Asp Ile Gly Leu Gly Tyr Pro Asn Gly Asn
        290                 295                 300

Gln Gly Trp Gly Arg Val Thr Leu Asp Lys Ser Leu Asn Val Ala Tyr
305                 310                 315                 320

Val Asn Glu Ser Ser Ser Leu Ser Thr Ser Gln Lys Ala Thr Tyr Ser
            325                 330                 335

Phe Thr Ala Thr Ala Gly Lys Pro Leu Lys Ile Ser Leu Val Trp Ser
            340                 345                 350

Asp Ala Pro Ala Ser Thr Thr Ala Ser Val Thr Leu Val Asn Asp Leu
        355                 360                 365

Asp Leu Val Ile Thr Ala Pro Asn Gly Thr Gln Tyr Val Gly Asn Asp
        370                 375                 380

Phe Ser Ala Pro Tyr Asn Asn Asn Trp Asp Gly Arg Asn Asn Val Glu
385                 390                 395                 400

Asn Val Phe Ile Ser Ala Pro Gln Ser Gly Thr Tyr Thr Val Glu Val
            405                 410                 415

Gln Ala Tyr Asn Val Pro Val Gly Pro Gln Asn Phe Ser Leu Ala Ile
            420                 425                 430

Val Asn

<210> SEQ ID NO 3
<211> LENGTH: 1305
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(1305)

<400> SEQUENCE: 3 aat gac gtg gcc cgt ggc att gtg aaa gca gac gtc gca caa aat aac    48
Asn Asp Val Ala Arg Gly Ile Val Lys Ala Asp Val Ala Gln Asn Asn
1               5                   10                  15 ttt ggc tta tat gga caa gga cag att gta gca gtt gct gat act ggg    96
Phe Gly Leu Tyr Gly Gln Gly Gln Ile Val Ala Val Ala Asp Thr Gly
            20                  25                  30 ctt gat aca gga aga aat gac agt tcg atg cat gaa gca ttc cgc ggg   144
Leu Asp Thr Gly Arg Asn Asp Ser Ser Met His Glu Ala Phe Arg Gly
```

```
                     35                  40                  45
aaa att acg gca tta tat gca cta ggt cgc act aat aat gcc aat gat      192
Lys Ile Thr Ala Leu Tyr Ala Leu Gly Arg Thr Asn Asn Ala Asn Asp
 50                  55                  60 aca cac ggt cat ggt acg cat gtg gcg ggc tct gta tta gga aac ggc      240
Thr His Gly His Gly Thr His Val Ala Gly Ser Val Leu Gly Asn Gly
 65                  70                  75                  80 tcc act aat aaa gga atg gca ccg cag gcg aat ctt gtc ttc caa tct      288
Ser Thr Asn Lys Gly Met Ala Pro Gln Ala Asn Leu Val Phe Gln Ser
                 85                  90                  95 atc atg gat agc ggt gga gga ctt gga ggt cta cct tcg aat ctg caa      336
Ile Met Asp Ser Gly Gly Gly Leu Gly Gly Leu Pro Ser Asn Leu Gln
            100                 105                 110 acc tta ttc agc caa gca tac agt gca ggt gcc aga att cat aca aac      384
Thr Leu Phe Ser Gln Ala Tyr Ser Ala Gly Ala Arg Ile His Thr Asn
        115                 120                 125 tcc tgg gga gca gcg gta aat ggg gct tac acg aca gat tca agg aat      432
Ser Trp Gly Ala Ala Val Asn Gly Ala Tyr Thr Thr Asp Ser Arg Asn
    130                 135                 140 gtg gat gac tat gta cga aaa aat gat atg acg att ctt ttc gct gcc      480
Val Asp Asp Tyr Val Arg Lys Asn Asp Met Thr Ile Leu Phe Ala Ala
145                 150                 155                 160 gga aat gaa gga ccg aac ggc gga acc atc agt gca cca ggt aca gct      528
Gly Asn Glu Gly Pro Asn Gly Gly Thr Ile Ser Ala Pro Gly Thr Ala
                165                 170                 175 aaa aat gcc ata aca gtc ggg gct acg gaa aac ctc cgt cca agc ttc      576
Lys Asn Ala Ile Thr Val Gly Ala Thr Glu Asn Leu Arg Pro Ser Phe
            180                 185                 190 ggg tcc tat gcg gat aac atc aac cat gtg gca cag ttt tct tca cgc      624
Gly Ser Tyr Ala Asp Asn Ile Asn His Val Ala Gln Phe Ser Ser Arg
        195                 200                 205 gga cct aca aag gat gga cga atc aag ccg gac gtc atg gct ccg gga      672
Gly Pro Thr Lys Asp Gly Arg Ile Lys Pro Asp Val Met Ala Pro Gly
    210                 215                 220 acg ttc att tta tca gca aga tcc tct ctt gca ccg gat tcg tca ttc      720
Thr Phe Ile Leu Ser Ala Arg Ser Ser Leu Ala Pro Asp Ser Ser Phe
225                 230                 235                 240 tgg gcg aac cat gat agc aaa tat gct tat atg ggt gga acg tcc atg      768
Trp Ala Asn His Asp Ser Lys Tyr Ala Tyr Met Gly Gly Thr Ser Met
                245                 250                 255 gcc acg cca att gtt gca gga aac gtg gca cag ctt cgt gag cat ttt      816
Ala Thr Pro Ile Val Ala Gly Asn Val Ala Gln Leu Arg Glu His Phe
            260                 265                 270 gtg aaa aat aga ggc atc aca cca aag cca tct tta tta aaa gcg gca      864
Val Lys Asn Arg Gly Ile Thr Pro Lys Pro Ser Leu Leu Lys Ala Ala
        275                 280                 285 ctg att gct ggt gcg gct gac atc ggg ctt ggc tac ccg aac gga aac      912
Leu Ile Ala Gly Ala Ala Asp Ile Gly Leu Gly Tyr Pro Asn Gly Asn
    290                 295                 300 caa gga tgg ggc cga gtg aca ttg gat aaa tcg ctg aac gtt gcc tat      960
Gln Gly Trp Gly Arg Val Thr Leu Asp Lys Ser Leu Asn Val Ala Tyr
305                 310                 315                 320 gtg aac gaa tct agt tct cta tca act agt caa aaa gcg aca tac tcg     1008
Val Asn Glu Ser Ser Ser Leu Ser Thr Ser Gln Lys Ala Thr Tyr Ser
                325                 330                 335 ttt aca gct act gcc ggc aag ccg ctg aag atc tcc ctg gta tgg tct     1056
Phe Thr Ala Thr Ala Gly Lys Pro Leu Lys Ile Ser Leu Val Trp Ser
            340                 345                 350 gat gca cca gct agc aca act gct tcc gta acg ctc gtc aat gat ttg     1104
Asp Ala Pro Ala Ser Thr Thr Ala Ser Val Thr Leu Val Asn Asp Leu
```

```
                355                 360                 365
gac ctt gtc att acc gct cca aat ggc aca caa tat gtt gga aat gac    1152
Asp Leu Val Ile Thr Ala Pro Asn Gly Thr Gln Tyr Val Gly Asn Asp
370                 375                 380 ttt tct gct cca tac aat aat aac tgg gat ggc cgc aac aac gtg gaa    1200
Phe Ser Ala Pro Tyr Asn Asn Asn Trp Asp Gly Arg Asn Asn Val Glu
385                 390                 395                 400 aat gtg ttt atc aat gct cct caa agc gga acg tat aca gtc gaa gtg    1248
Asn Val Phe Ile Asn Ala Pro Gln Ser Gly Thr Tyr Thr Val Glu Val
            405                 410                 415 cag gct tac aat gta cca gta ggt ccg caa acc ttt tct tta gcg att    1296
Gln Ala Tyr Asn Val Pro Val Gly Pro Gln Thr Phe Ser Leu Ala Ile
            420                 425                 430 gta cat taa                                                         1305
Val His <210> SEQ ID NO 4
<211> LENGTH: 434
<212> TYPE: PRT
<213> ORGANISM: Artificial Sequence
<220> FEATURE:
<223> OTHER INFORMATION: Synthetic Construct

<400> SEQUENCE: 4

Asn Asp Val Ala Arg Gly Ile Val Lys Ala Asp Val Ala Gln Asn Asn
1               5                   10                  15

Phe Gly Leu Tyr Gly Gln Gly Gln Ile Val Ala Val Ala Asp Thr Gly
                20                  25                  30

Leu Asp Thr Gly Arg Asn Asp Ser Ser Met His Glu Ala Phe Arg Gly
            35                  40                  45

Lys Ile Thr Ala Leu Tyr Ala Leu Gly Arg Thr Asn Asn Ala Asn Asp
    50                  55                  60

Thr His Gly His Gly Thr His Val Ala Gly Ser Val Leu Gly Asn Gly
65                  70                  75                  80

Ser Thr Asn Lys Gly Met Ala Pro Gln Ala Asn Leu Val Phe Gln Ser
                85                  90                  95

Ile Met Asp Ser Gly Gly Gly Leu Gly Gly Leu Pro Ser Asn Leu Gln
                100                 105                 110

Thr Leu Phe Ser Gln Ala Tyr Ser Ala Gly Ala Arg Ile His Thr Asn
            115                 120                 125

Ser Trp Gly Ala Ala Val Asn Gly Ala Tyr Thr Thr Asp Ser Arg Asn
    130                 135                 140

Val Asp Asp Tyr Val Arg Lys Asn Asp Met Thr Ile Leu Phe Ala Ala
145                 150                 155                 160

Gly Asn Glu Gly Pro Asn Gly Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190

Gly Ser Tyr Ala Asp Asn Ile Asn His Val Ala Gln Phe Ser Ser Arg
        195                 200                 205

Gly Pro Thr Lys Asp Gly Arg Ile Lys Pro Asp Val Met Ala Pro Gly
    210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
```

-continued

```
                260                 265                 270
Val Lys Asn Arg Gly Ile Thr Pro Lys Pro Ser Leu Leu Lys Ala Ala
        275                 280                 285
Leu Ile Ala Gly Ala Ala Asp Ile Gly Leu Gly Tyr Pro Asn Gly Asn
    290                 295                 300
Gln Gly Trp Gly Arg Val Thr Leu Asp Lys Ser Leu Asn Val Ala Tyr
305                 310                 315                 320
Val Asn Glu Ser Ser Ser Leu Ser Thr Ser Gln Lys Ala Thr Tyr Ser
                325                 330                 335
Phe Thr Ala Thr Ala Gly Lys Pro Leu Lys Ile Ser Leu Val Trp Ser
            340                 345                 350
Asp Ala Pro Ala Ser Thr Thr Ala Ser Val Thr Leu Val Asn Asp Leu
        355                 360                 365
Asp Leu Val Ile Thr Ala Pro Asn Gly Thr Gln Tyr Val Gly Asn Asp
    370                 375                 380
Phe Ser Ala Pro Tyr Asn Asn Asn Trp Asp Gly Arg Asn Asn Val Glu
385                 390                 395                 400
Asn Val Phe Ile Asn Ala Pro Gln Ser Gly Thr Tyr Thr Val Glu Val
                405                 410                 415
Gln Ala Tyr Asn Val Pro Val Gly Pro Gln Thr Phe Ser Leu Ala Ile
            420                 425                 430
Val His
```

<210> SEQ ID NO 5
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(2)
<223> OTHER INFORMATION: n in position 2 is inosine
<220> FEATURE:
<221> NAME/KEY: misc_feature
<222> LOCATION: (14)..(14)
<223> OTHER INFORMATION: n in position 14 is inosine

<400> SEQUENCE: 5
cnatgcatga agcnttccgc gg                                            22

<210> SEQ ID NO 6
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(2)
<223> OTHER INFORMATION: n in position 2 is inosine
<220> FEATURE:
<221> NAME/KEY: misc_feature
<222> LOCATION: (11)..(11)
<223> OTHER INFORMATION: n in position 11 is inosine
<220> FEATURE:
<221> NAME/KEY: misc_feature
<222> LOCATION: (13)..(13)
<223> OTHER INFORMATION: n in position 13 is inosine

<400> SEQUENCE: 6
cnacgttgtt ncngccatcc c                                             21

<210> SEQ ID NO 7

```
<211> LENGTH: 22
<212> TYPE: DNA
<213> ORGANISM: Artificial Sequence
<220> FEATURE:
<223> OTHER INFORMATION: Primer

<400> SEQUENCE: 7
ccgaacggaa accaaggatg gg                                                  22

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
ggagccgttt cctaatacag ag                                                  22

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ttggaccttg tcattaccgc                                                     20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
agacctccaa gtcctccacc                                                     20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
cattgcttgc tgcgtattgg                                                     20

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
ccgcggaatg cttcatgcat cg                                                  22

<210> SEQ ID NO 13
<211> LENGTH: 30
<212> TYPE: DNA
<213> ORGANISM: Artificial Sequence
<220> FEATURE:
<223> OTHER INFORMATION: Primer PEP200

<400> SEQUENCE: 13
```

```
gttcatcgat cttctactat tggggcgaac                                          30

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
gggatggcag aaacaacgtg g                                                   21

<210> SEQ ID NO 15
<211> LENGTH: 35
<212> TYPE: DNA
<213> ORGANISM: Artificial Sequence
<220> FEATURE:
<223> OTHER INFORMATION: Primer

<400> SEQUENCE: 15
ttaaacgcgt taatgtaca atcgctaaag aaaag                                     35

<210> SEQ ID NO 16
<211> LENGTH: 30
<212> TYPE: DNA
<213> ORGANISM: Artificial Sequence
<220> FEATURE:
<223> OTHER INFORMATION: Primer

<400> SEQUENCE: 16
ttaaacgcgt ttagtttaca attgccaacg                                          30

<210> SEQ ID NO 17
<211> LENGTH: 22
<212> TYPE: DNA
<213> ORGANISM: Artificial Sequence
<220> FEATURE:
<223> OTHER INFORMATION: CDJ120 SOEF Primer
<220> FEATURE:
<221> NAME/KEY: misc_feature
<222> LOCATION: (6)..(6)
<223> OTHER INFORMATION: n in position 6 is inosine
<220> FEATURE:
<221> NAME/KEY: misc_feature
<222> LOCATION: (15)..(15)
<223> OTHER INFORMATION: n in position 15 is inosine
<220> FEATURE:
<221> NAME/KEY: misc_feature
<222> LOCATION: (18)..(18)
<223> OTHER INFORMATION: n in position 18 is inosine

<400> SEQUENCE: 17
aatgangtgg cccgnggnat tg                                                  22

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
caatgccacg ggccacgtca tt                                                  22
```